(12) United States Patent
Hogg et al.

(10) Patent No.: US 7,806,899 B2
(45) Date of Patent: Oct. 5, 2010

(54) PATELLAR RESECTION TOOL

(76) Inventors: Alex Hogg, 14 Second Avenue, Bardsey, Leeds (GB) LS17 9BQ; Michael Lim, Cad Potential Europe U.K. Limited, Creative Industries Care, Glaisher Drive, Wolverhampton (GB) WV10 9TG; Carl F. Livorsi, 24 County Rd., Lakeville, MA (US) 02347; Liam Rowley, 12 Oakbank Drive, Keighley (GB) BD22 7DX; Phillip G. Withee, 79 Kellogg St., Fall River, MA (US) 02724

( * ) Notice: Subject to any disclaimer, the term of this patent is extended or adjusted under 35 U.S.C. 154(b) by 723 days.

(21) Appl. No.: 11/436,331

(22) Filed: May 18, 2006
(Under 37 CFR 1.47)

(65) Prior Publication Data
US 2007/0162031 A1 Jul. 12, 2007

(51) Int. Cl.
*A61B 17/58* (2006.01)
(52) U.S. Cl. .......................... 606/88; 606/86 R; 606/87
(58) Field of Classification Search .................. 606/57, 606/83, 245, 247, 86, 87, 88, 90, 96, 99, 606/102, 103, 105, 205, 206, 207, 208, 210; 81/342
See application file for complete search history.

(56) References Cited

U.S. PATENT DOCUMENTS

| | | | | |
|---|---|---|---|---|
| 1,557,370 | A * | 10/1925 | Lane | 29/270 |
| 2,507,710 | A * | 5/1950 | Grosso | 606/205 |
| 3,742,957 | A * | 7/1973 | White | 606/208 |
| 4,633,862 | A * | 1/1987 | Petersen | 606/88 |
| 5,108,401 | A * | 4/1992 | Insall et al. | 606/79 |
| 5,147,365 | A * | 9/1992 | Whitlock et al. | 606/88 |
| 5,250,050 | A * | 10/1993 | Poggie et al. | 606/79 |
| 5,415,663 | A * | 5/1995 | Luckman et al. | 606/86 R |
| 5,542,947 | A * | 8/1996 | Treacy | 606/88 |
| 5,931,777 | A * | 8/1999 | Sava | 600/213 |
| 6,610,074 | B2 * | 8/2003 | Santilli | 606/158 |
| 6,716,218 | B2 * | 4/2004 | Holmes et al. | 606/105 |
| 2002/0133157 | A1 * | 9/2002 | Sterett et al. | 606/69 |
| 2004/0039397 | A1 | 2/2004 | Weber et al. | |

FOREIGN PATENT DOCUMENTS

| | | |
|---|---|---|
| EP | 1044653 A | 10/2000 |
| GB | 2146900 A | 5/1985 |

OTHER PUBLICATIONS

European Search Report dated Aug. 31, 2006.
UK Search Report dated Aug. 22, 2005.

* cited by examiner

*Primary Examiner*—Eduardo C Robert
*Assistant Examiner*—Lynnsy Schneider

(57) ABSTRACT

A patellar resection tool has first and second gripping members adapted for relative movement between a closed position in which the patella can be held between the gripping members and an open position in which the patella can be released. The tool also has first and second handle members connected to the first and second gripping members respectively, for moving the gripping members between the open and closed positions. The first and second handle members are constrained for relative movement in a first plane and the first and second gripping members are constrained for relative movement in a second plane which is not parallel to the first plane. This allows the tool to be used in a minimally invasive surgical technique in which a patella is everted by an angle less than 90° without obstructing access to the patella.

13 Claims, 6 Drawing Sheets

PATELLAR RESECTION TOOL

The present invention relates a patellar resection tool for gripping a patella and for guiding a bone saw during resection of the patella.

During knee replacement surgery it is necessary to resect the patella to allow it to receive an implant. Conventional knee surgery techniques use a relatively large incision which allows a surgeon access to the patellar. The surgeon then uses a patellar resection guide to clamp and hold the patellar and evert it through approximately 180° to a position at which it is sufficiently exposed that a bone saw can be used for resection. The resection guide is then used to guide the bone saw.

Known devices for use in surgery have a form resembling a pair of pliers with a pair of jaws adapted to hold a patella and handles for opening and closing the jaws. The handles and the jaws are pivotally connected at a single point so that the jaws and the handles both operate in a plane perpendicular to the axis of the pivot. One example of such a device is described in WO-A-96/35379.

Recently, there has been a desire to develop minimally invasive surgical techniques for knee surgery. In a minimally invasive technique the eversion of the patella is preferably less than 90°. Conventional patellar resection tools such as that described in WO-A-96/35379 are difficult to use in this situation because the handles are difficult to use when the patella is everted by an angle less than 90°.

In view of this, the present invention provides a patellar resection guide in which the handles operate in a plane which is not parallel to the plane in which the jaws operate. This enables easier use of the tool because the handles are located in a more ergonomic position for when the angle of eversion is less than 90°.

According to the present invention, there is provided a patellar resection tool comprising:
  first and second gripping members adapted for relative movement between a closed position in which the patella can be held between the gripping members and an open position in which the patella can be released; and
  first and second handle members connected to the first and second gripping members respectively, for moving the gripping members between the open and closed positions;
  in which the first and second handle members are constrained for relative movement in a first plane and the first and second gripping members are constrained for relative movement in a second plane which is not parallel to the first plane.

The present invention therefore allows easier and more ergonomic use of the tool when the patella has been everted by less than 90°. Another benefit is that because the handles move in a plane which is not parallel to the plane in which the jaws move, a surgeon can have better visibility of the incision when the resection guide is first used to grip the patella, before eversion has taken place. A further benefit is that the position of handles ensures that access to the patella is not restricted by the handles when the patella has been everted by an angle less than 90°.

The gripping members may be substantially planar to define a cutting surface for resection.

Preferably, the first and second gripping members are connected for pivotal movement about a fulcrum whose axis is substantially perpendicular to the second plane. This allows them to move relative to each other in the second plane.

Preferably, the first and second handle members are connected for pivotal movement about a fulcrum whose axis is substantially perpendicular to the first plane. This allows them to move relative to each other in the first plane.

Preferably, the first and second handle members are connected to the first and second gripping members by respective first and second link members. This allows movement of the handle members in the first plane to be transferred to the gripping members in the second plane.

Preferably, each link member has a first end attached to the handle member by a rotational joint about an axis substantially perpendicular to the first plane, and a second end attached to the gripping member by a rotational joint about an axis substantially perpendicular to the second plane. The joint is therefore given two degrees of freedom to allow the gripping members to have purely translational movement in the second plane. Without such a joint the gripping members will have a component of rotational movement relative to the second plane, as well as a translational movement.

The rotational joints referred to above may be a pivotal connection, a pin joint, or any other connection which allows relative movement of the two items connected about an axis.

Preferably, the resection tool further comprises a guide member mounted in a plane substantially parallel to the second plane, and wherein the guide member is fixed relative to one of the first and second gripping members. The guide member can be used to guide a bone saw when the resection guide has been used to evert the patellar to the correct position.

Preferably, the guide member in combination with at least one of the first and second gripping members delimits an opening for receiving and guiding a bone saw.

Preferably, the resection tool further comprises a stylus member which can be removably attached to the guide member. The stylus member can be used to indicate a particular depth of resection. When fitted to the resection guide the stylus member is used to contact a surface of the patellar to ensure that the guide is in the correct position for the desired depth of resection. In alternate embodiments a range of different styli for indicating different depths of resection can be provided.

Preferably, the gripping members are biassed towards the open position. The biassing may be achieved by a resilient member, preferably a spring, although other resilient materials, such as an elastomer may also be used. The resilient member may act directly or indirectly on the gripping members, although it is preferred for it to act indirectly on the gripping members by biassing the handle members apart from each other.

In one embodiment, the resection guide further comprises a ratchet member mounted on the first handle member, the ratchet member having a plurality of teeth which can each engage the second handle member. The ratchet member can then maintain the separation of the handle members at a predetermined position and counteract the biassing force applied by the resilient means.

Preferably, the ratchet member is made of a resilient material which biasses the ratchet member towards the second handle member. This allows the ratchet to be released simply be applying a force against the biassing force provided by the resilient material. This force is preferably sufficiently low that a surgeon can deflect the ratchet member by hand without requiring any further instruments to allow the ratchet to be released easily. The resilient material is preferably stainless steel, although other metals, alloys or plastics with elastic properties could also be used.

Preferably, the second handle member comprises an opening extending through it for receiving the ratchet member and wherein each of the plurality of teeth can engage with an edge of the slot.

Preferably, the ratchet member has an arcuate shape and the spacing between adjacent ones of the plurality of teeth is approximately 1° to 2°, preferably approximately 1.5°. This allows a fine degree of control over the separation of the handle members and hence the gripping members while also allowing the teeth to be large enough to have sufficient strength to substantially avoid deformation or shearing when they are engaged with the second handle member.

Preferably, the height of the plurality of teeth is approximately 0.25 mm to 1 mm, preferably approximately 0.5 mm. The teeth are then large enough to have sufficient strength and yet also small enough to enable only a relatively small movement of the ratchet member to disengage the teeth from the second handle member.

Preferably, the resection tool further comprises a locking member for preventing disengagement of the ratchet member from the second handle member, thereby locking the handle members in a predetermined position. This is particularly advantageous for preventing disengagement when a ratchet member made from a resilient material is used.

In another embodiment, the resection tool may further comprise:
a ratchet member extending from the first handle member, the ratchet member having a plurality of teeth; and
a pawl member pivotally mounted on the second handle member and arranged to engage the spaces between the teeth of the ratchet member.

Embodiments of the invention will now be described by way of example only with reference to the accompanying drawings, in which.

Figure 1:
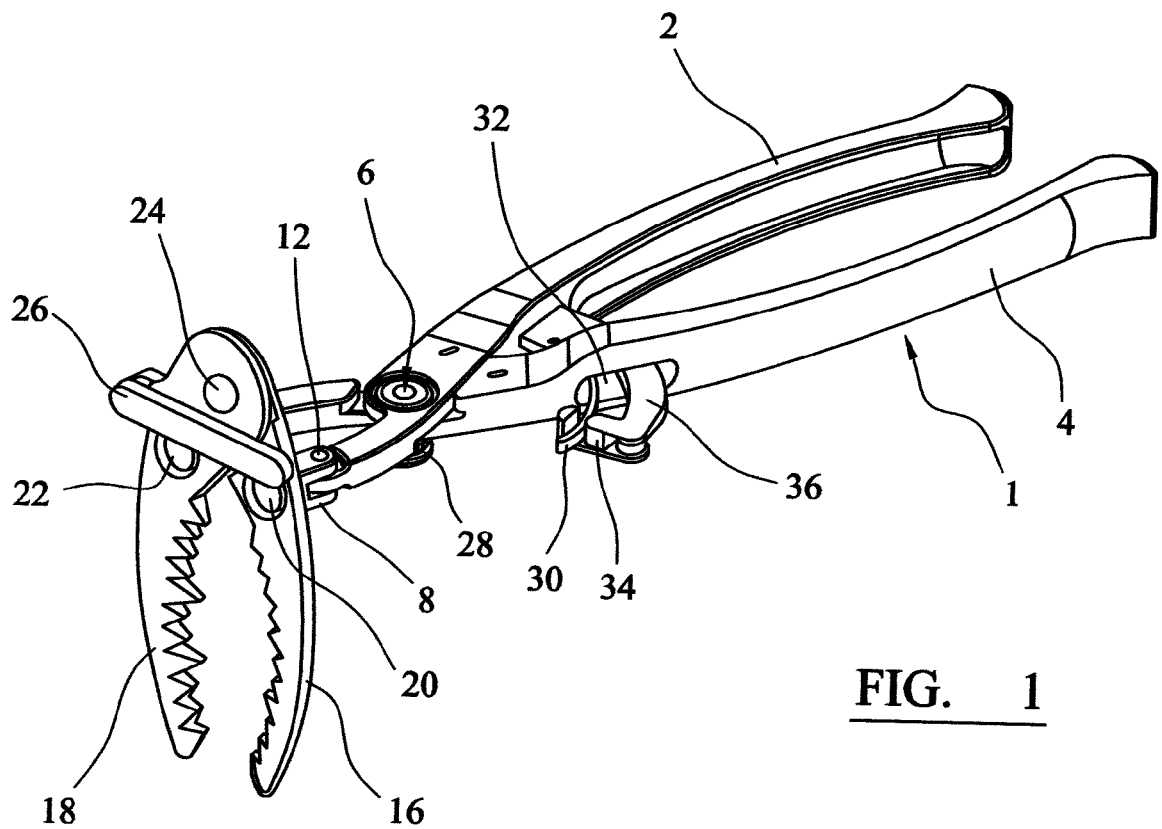
FIG. 1 depicts a perspective view of an embodiment of the present invention.
Figure 2:
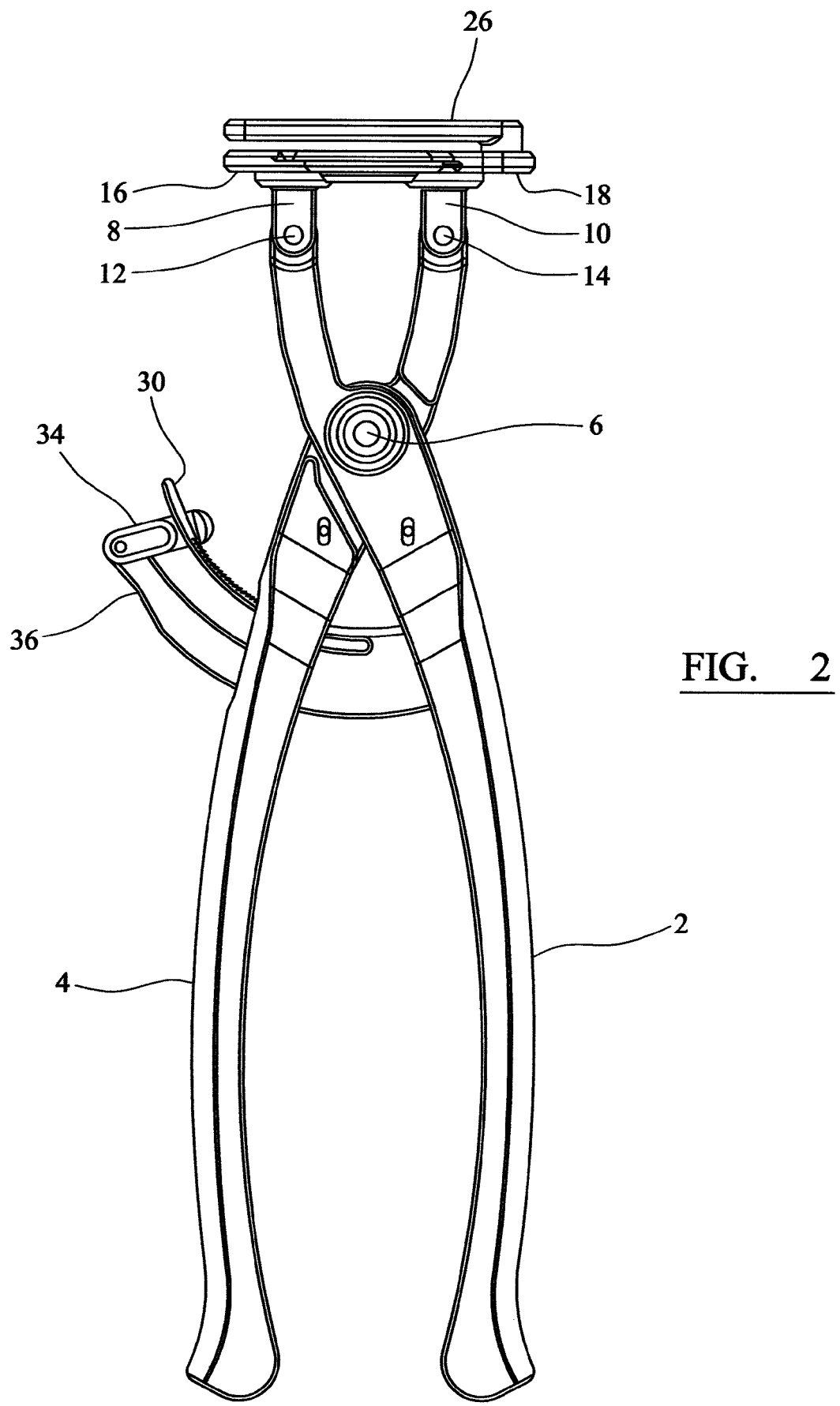
FIG. 2 depicts a top view of the embodiment of FIG. 1.
Figure 3:
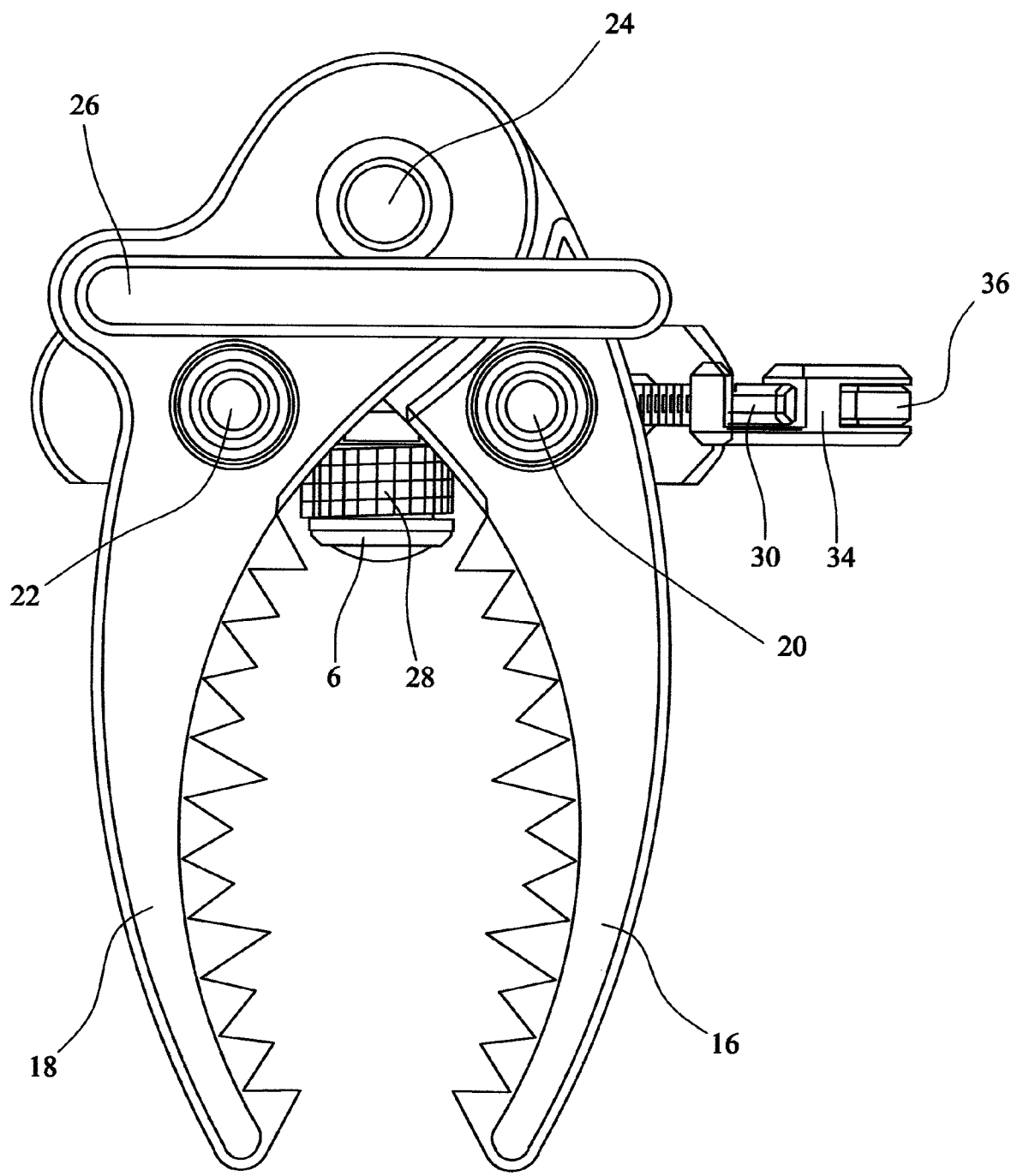
FIG. 3 depicts an end view of the embodiment of FIG. 1.

A first embodiment of the patellar resection tool 1 of the present invention is depicted in FIG. 1. FIG. 2 depicts a top view and FIG. 3 an end view of the embodiment of FIG. 1. The patellar resection tool 1 comprises first and second handle members 2, 4 which are connected for pivotal movement by a first rotational joint 6. In this embodiment the first rotational joint 6 is a pin joint, although other forms of connection can also be used. The first rotational joint 6 allows the handle members 2,4 to move relative to each other in a first plane which is generally perpendicular to the axis of the first rotational joint 6.

The handle members 2, 4 are connected to a proximal end of respective link members 8, 10 by second and third rotational joints 12, 14. These second and third rotational joints 12, 14 are also pin joints and have axes which are substantially parallel to the axis of the rotational joint 6.

A pair of gripper members 16, 18 are attached to the distal end of the link members 8, 10 by fourth and fifth rotational joints 20, 22. A plurality of teeth are formed on one edge of each gripper member 16, 18 to enable them to grasp a patella when the grippers are moved towards each other into a closed position. The gripper members 16, 18 are substantially planar to define a smooth cutting surface for resection and are connected together for pivotal movement by a sixth rotational joint 24. The sixth rotational joint 24 is also a pin joint and has an axis substantially perpendicular to a second plane defined by the gripper members 16, 18. The gripper members can therefore move relative to each other within the second plane. In order to allow the gripper members to move without a rotational component out of the second plane, the fourth and fifth rotational joints 20, 22 to the link member each have an axis substantially parallel to the axis of the sixth rotational joint 24. The second plane is at an angle of approximately 90° to the first plane.

A guide member 26 is attached to one of the gripper members 16, 18. This has a substantially planar form and defines a slot together with the substantially planar surfaces of the gripper members 16, 18 into which a cutting blade can be inserted for resection.

A spring 28 is attached the handle members 2, 4 around their common rotational joint 6. The spring 28 acts to bias the handle member 2, 4 apart, and hence will indirectly bias the gripper members 16, 18 apart.

To allow the handle members to be maintained at a certain position relative to each other, against the biassing force provided by the spring 28, a ratchet member 30 is provided and attached to the first handle member 2. An opening 32 is formed in the second handle member 4 to receive the ratchet member 30. To allow the ratchet member 30 to pass smoothly through the opening 32 at all relative positions of the handle members 2, 4, the ratchet member 30 has an arcuate form with a radius of curvature defined by its distance from the common rotational joint 6.

A plurality of teeth are provided on the ratchet member 30. They are spaced approximately 1.5° apart from the radius of curvature and are about 0.5 mm high. These teeth engage with the edge of the opening 32 to act against the biassing force of the spring 28 and maintain the handle members 2, 4 a predetermined distance apart. In this embodiment the ratchet member 30 is formed from stainless steel. The resilient properties of the stainless bias the ratchet member 30 against an edge of the opening 32, engaging one of the teeth to activate the ratchet.

The dimensions of the ratchet member 30 are chosen such that it can be deflected away from the edge of the slot by an operator's hand without requiring any special tools. In this embodiment this is achieved by using a ratchet member which is approximately 1.5 mm thick, although this value will vary depending on the properties of the material from which the ratchet is made.

To prevent accidental release of the ratchet a locking member 34 is also provided. The locking member is attached to a projection 36 at the rear of the ratchet and can simply be rotated into a locking position (depicted in the Figures) in which it acts to prevent deflection of the ratchet member 30 so that the ratchet member's teeth are prevented from disengaging with the edge of the slot 32.

Figure 4:
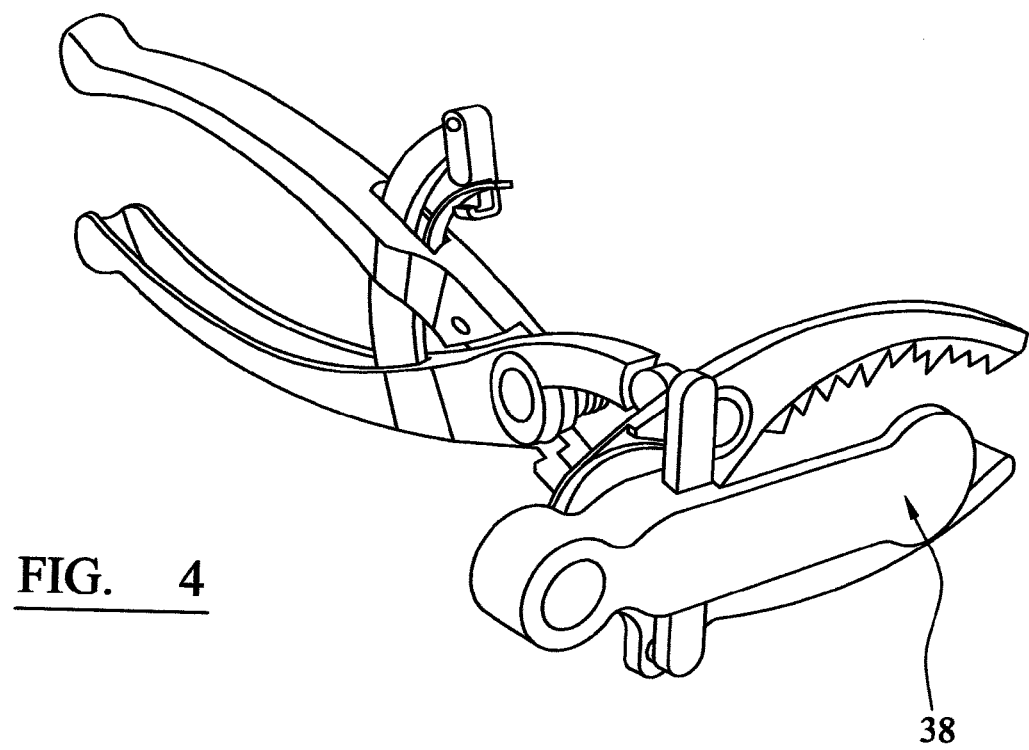
FIG. 4 depicts a perspective view of the embodiment of FIG. 1 with an optional stylus attached.

FIG. 4 depicts a perspective view of the embodiment with a stylus member 38 attached to the guide member 26. The stylus member is used by the surgeon to assist in positioning the patellar resection tool for the desired depth of resection. A number of different styli corresponding to different depths of resection can be provided.

The patellar resection tool is manufactured from 17/4 Stainless steel, although other medical grade materials including other metals and alloys may also be used.

In use, a surgeon will first remove the locking member 34 from the ratchet member 30 and then release the ratchet member 30 to open the gripper members. The resection tool 1 will then be inserted through an incision in the knee and positioned to grip the patella. This positioning may be carried out with the aid of the stylus member 38 to ensure accurate positioning of the resection tool.

Next the surgeon squeezes the handle members 2, 4 towards each other, against the biassing force of the spring 28. This causes the teeth of the gripper members 16, 18 to contact and grip the patella. Once the patella is firmly held by the gripper members 16, 18 the ratchet member 30 will maintain the handle members 2, 4, and hence the gripper members 16, 18, at the desired separation. In order to prevent accidental release of the ratchet the surgeon can rotate the locking member 34 into the locked position.

Now that the resection tool is gripping the patella firmly, the surgeon can evert the patellar to allow it to be resected. The angle of the handle members 2, 4 relative to the gripper members 16, 18 ensure that they do not obstruct access to the patella when the patella is everted by less than 90°.

The patella is resected by inserting a cutting edge, for example a reciprocating blade, between the guide member 26 and the planar surface of the gripping members 16, 18. The resected surface is therefore defined by the planar surface of the gripping members 16, 18. The arrangement of the link members ensures that the planar surfaces of the gripping members are always in the same plane to allow accurate resection. Without the link members the gripping members would tend to rotate about an axis as they are opened and closed and therefore they would not necessarily both be in the same plane to allow accurate resection.

In alternate embodiments of the invention the angle between the first plane (of the handles) and the second plane (of the gripping members) can be other angles than 90°, provided that the first and the second plane are not parallel. The precise choice of angle will depend on the angle through which the patellar is everted and the surgical technique used for resection.

Figure 5:
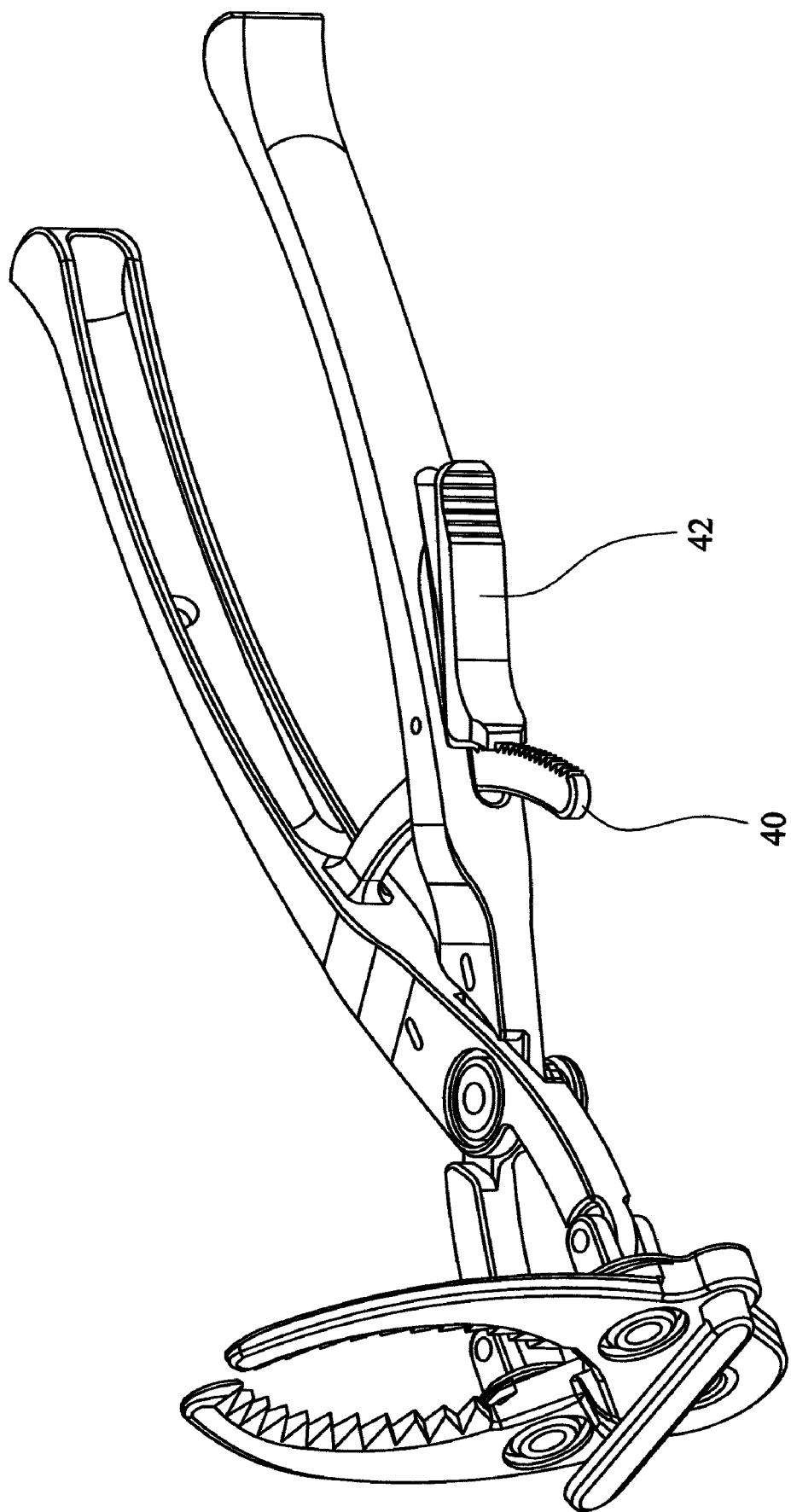
FIG. 5 depicts a perspective view of a further embodiment of the present invention.
Figure 6:
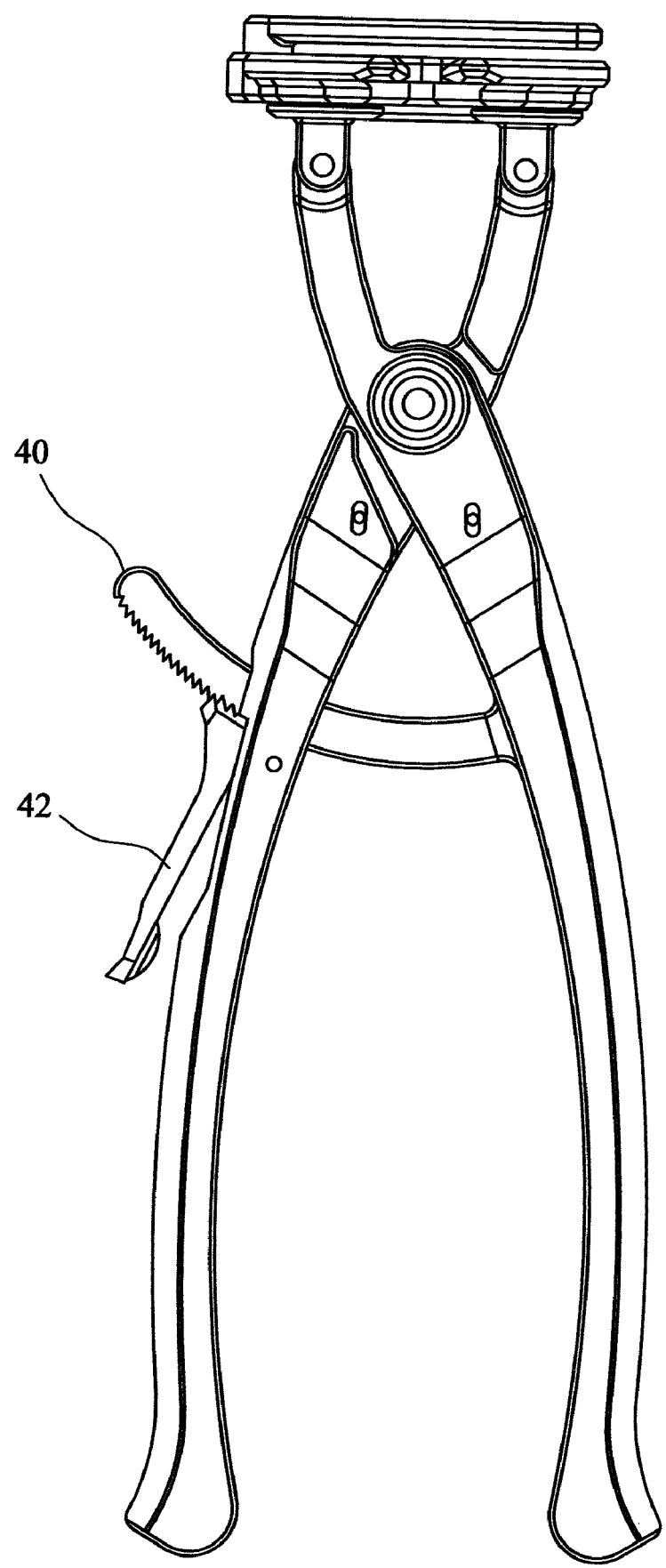
FIG. 6 depicts a plan view of the embodiment of FIG. 5.

A further embodiment of the present invention is depicted in perspective view in FIG. 5 and in plan view in FIG. 6. The construction of this embodiment is the same as the first, save as described below.

Figure 7:
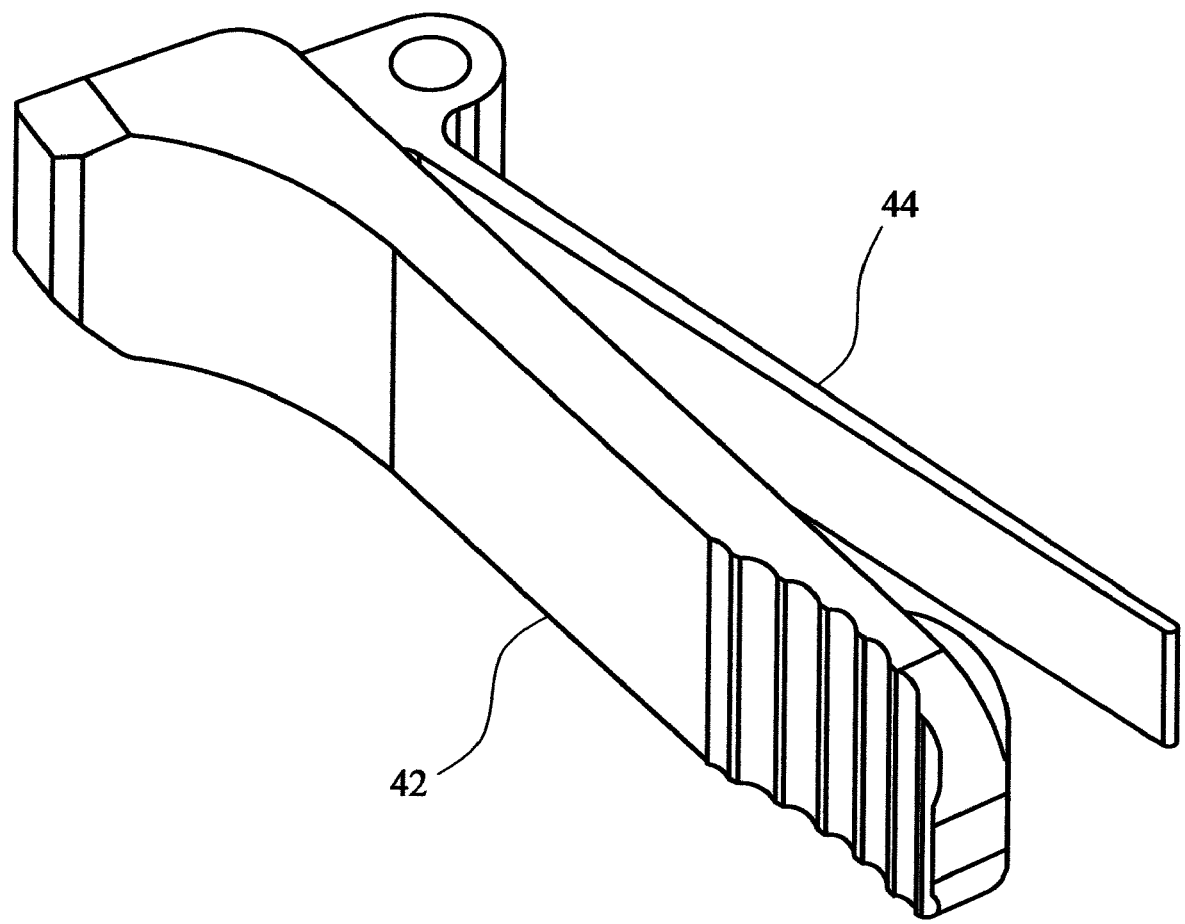
FIG. 7 depicts a perspective view of the pawl member of the embodiment of FIG. 5.

In this embodiment a generally arcuate ratchet member 40 extends from one of the handles. The ratchet member 40 is engaged by a pawl member 42 that is pivotally mounted on the other of the handles. A resilient means biases the pawl member 42 into engagement with the teeth of the ratchet member. The resilient means may be a spring, such as a leaf spring, or an elastomer. In this embodiment, the resilient means is a leaf spring. FIG. 7 depicts the pawl member 42 in isolation from the patellar resection tool. The leaf spring 44 is formed integrally with the pawl member 42.

In order to release the ratchet of this embodiment, the user can simply pivot the pawl member 42 out of engagement with the ratchet member 40, acting against the force applied by the resilient means.

In this embodiment a locking member is not provided. However, alternate embodiments may comprise a locking mechanism to prevent accidental release of the ratchet.

The invention claimed is:

1. A tool for resecting a patella, comprising:
   a first gripping member and a second gripping member adapted for relative movement between a closed position, wherein the patella can be held between the first gripping member and the second gripping member, and an open position, wherein the patella can be released from the first gripping member and the second gripping member, the first gripping member and the second gripping member each have a proximal end and a distal end, and the first gripping member and the second gripping member are pivotally connected to one another at their respective proximal ends; and
   a first handle member and a second handle member, each having a proximal end and a distal end, the first handle member and the second handle member being pivotally connected to one another at a location intermediate their respective proximal and distal ends, the first handle member and the second handle member being connected at their respective distal ends to the first gripping member and the second gripping member, respectively, for moving the gripping members between the open position and the closed position; wherein the first handle member and the second handle member are constrained for relative movement in a first plane, the first gripping member and the second gripping member are constrained for; a first link member connecting the first handle member and the first gripping member; a second link member connecting the second handle member and the second gripping member; and wherein each of the first link member and the second link member has a first end attached to the first handle member and second handle member, respectively, by a rotational joint about an axis substantially perpendicular to the first plane, and a second end attached to the first gripping member and the second gripping member, respectively, by a rotational joint about an axis substantially perpendicular to the second plane.

2. The tool of claim 1, further comprising a guide member mounted in a plane substantially parallel to the second plane, and wherein the guide member is fixed relative to one of the first gripping member and the second gripping member.

3. The tool of claim 2, wherein the guide member in combination with at least one of the first gripping member and the second gripping member delimits an opening sized to receive and guide a bone saw.

4. The tool of claim 2, further comprising a stylus member which can be removably attached to the guide member.

5. The tool of claim 1, wherein the first gripping member and the second gripping member are biased towards the open position.

6. The tool of claim 1, further comprising a ratchet member mounted on the first handle member, the ratchet member having a plurality of teeth that are configured to engage the second handle member.

7. The tool of claim 1, further comprising:
   a ratchet member extending from the first handle member; and
   a pawl member pivotally mounted on the second handle member and configured to engage to the ratchet member.

8. The tool of claim 1, wherein the first gripping member and the second gripping member are pivotally connected to one another about an axis that is substantially perpendicular to the second plane.

9. The tool of claim 1, wherein the first gripping member and the second gripping member each have a proximal end and a distal end, and the first handle member and the second handle member are connected to the first gripping member and the second gripping member at a location intermediate of the respective proximal and distal ends of the first gripping member and the second gripping member.

10. A patellar resection tool for resecting a patella, comprising:
   a first handle member and a second handle member, each having a proximal end and a distal end, the first handle member and the second handle member being pivotally connected to one another about a first axis;

a first link member pivotally connected to the first handle member about a second axis;

a second link member pivotally connected to the second handle member about a third axis;

a first gripping member and a second gripping member being pivotally connected to one another about a fourth axis and adapted for relative movement between a closed position, wherein the patella can be held between the first gripping member and the second gripping member, and an open position, wherein the patella can be released from the first gripping member and the second gripping member, the first gripping member being pivotally connected to the first link member about a fifth axis, the second gripping member being pivotally connected to the second link member about a sixth axis;

wherein the first handle member and the second handle member are constrained for relative movement in a first plane, and the first gripping member and the second gripping member are constrained for relative movement in a second plane that is not parallel to the first plane;

wherein the first, second and third axes are substantially parallel to one another and the fourth, fifth and sixth axes are substantially parallel to one another; and wherein the first link member and the second link member pivot to permit the first gripping member and the second gripping member to pivot with respect to one another.

11. The tool of claim 10, wherein the first handle member and the second handle member are pivotally connected to one another at a location intermediate their respective proximal and distal ends.

12. The tool of claim 10, wherein the first gripping member and the second gripping member each have a proximal end and a distal end, and the first gripping member and the second gripping member are pivotally connected at their respective proximal ends.

13. The tool of claim 10, wherein the first gripping member and the second gripping member each have a proximal end and a distal end, and the first handle member and the second handle member are connected to the first gripping member and the second gripping member at a location intermediate of the respective proximal and distal ends of the first gripping member and the second gripping member.

* * * * *